(12) United States Patent
Lin et al.

(10) Patent No.: US 6,759,190 B2
(45) Date of Patent: Jul. 6, 2004

(54) TEST STRIP FOR DETECTION OF ANALYTE AND METHODS OF USE

(75) Inventors: Jinn-Nan Lin, San Diego, CA (US); Chia-Lin Wang, San Diego, CA (US)

(73) Assignee: Acon Laboratories, Inc., San Diego, CA (US)

( * ) Notice: Subject to any disclaimer, the term of this patent is extended or adjusted under 35 U.S.C. 154(b) by 67 days.

(21) Appl. No.: 10/173,457

(22) Filed: Jun. 15, 2002

(65) Prior Publication Data

US 2003/0232321 A1 Dec. 18, 2003

(51) Int. Cl.[7] .............................. C12Q 1/00; C12Q 1/54; C12Q 1/28; G01N 33/53
(52) U.S. Cl. ........................... 435/4; 435/970; 435/968; 435/14; 435/28; 422/69
(58) Field of Search .......................... 435/4, 970, 968, 435/14, 28; 422/69

(56) References Cited

U.S. PATENT DOCUMENTS

| | | | |
|---|---|---|---|
| 3,607,093 A | 9/1971 | Stone ............................. | 435/4 |
| 3,992,158 A | 11/1976 | Przybylowicz et al. ......... | 435/4 |
| 4,281,062 A | 7/1981 | Kallis ............................. | 435/4 |
| 4,303,753 A | 12/1981 | Lam ............................... | 435/4 |
| 4,748,114 A | 5/1988 | Kallies et al. ................... | 435/4 |
| 4,774,192 A | 9/1988 | Terminiello et al. ............ | 435/4 |
| 4,790,979 A | 12/1988 | Terminiello et al. ............ | 435/4 |
| 4,806,311 A | 2/1989 | Greenquist ..................... | 435/4 |
| 4,816,224 A | 3/1989 | Vogel et al. .................... | 435/4 |
| 4,877,580 A | 10/1989 | Arnowitz et al. ............... | 435/4 |
| 4,929,545 A | 5/1990 | Freitag ........................... | 435/4 |
| 4,935,346 A | 6/1990 | Phillips et al. .................. | 435/4 |
| 4,956,301 A | 9/1990 | Ismail et al. .................... | 435/4 |
| 5,049,487 A | 9/1991 | Phillips et al. .................. | 435/4 |
| 5,179,005 A | 1/1993 | Phillips et al. .................. | 435/4 |
| 5,185,247 A | 2/1993 | Ismail et al. .................... | 435/4 |
| 5,206,147 A | 4/1993 | Hoenes ........................... | 435/4 |
| 5,207,984 A | 5/1993 | Kheiri ............................. | 435/4 |
| 5,252,293 A | 10/1993 | Drbal et al. ..................... | 435/4 |
| 5,271,895 A | 12/1993 | McCroskey et al. ............. | 435/4 |
| 5,296,192 A | 3/1994 | Carroll et al. ................... | 435/4 |
| 5,304,468 A | 4/1994 | Phillips et al. .................. | 435/4 |
| 5,306,623 A | 4/1994 | Kiser et al. ..................... | 435/4 |
| 5,334,508 A | 8/1994 | Hoenes ........................... | 435/4 |
| 5,366,609 A | 11/1994 | White et al. .................... | 435/4 |
| 5,413,761 A | 5/1995 | Dulaney ......................... | 435/4 |
| 5,424,035 A | 6/1995 | Hones et al. .................... | 435/4 |
| 5,426,032 A | 6/1995 | Phillips et al. .................. | 435/4 |
| 5,521,060 A | 5/1996 | Hoenes et al. .................. | 435/4 |
| 5,526,120 A | 6/1996 | Jina et al. ....................... | 435/4 |
| 5,556,761 A | 9/1996 | Phillips .......................... | 435/4 |

(List continued on next page.)

FOREIGN PATENT DOCUMENTS

| | | |
|---|---|---|
| EP | 0 169 055 | 8/1991 |
| WO | 92/15863 | 9/1992 |
| WO | 99/35487 | 7/1999 |
| WO | 01/57239 | 1/2001 |

*Primary Examiner*—Louise N. Leary
(74) *Attorney, Agent, or Firm*—Foley & Lardner LLP

(57) ABSTRACT

One aspect of the present invention is a reagent test strip that includes: a) a top support layer including a sample aperture; b) a membrane that includes a reagent system for indicating the concentration of a target; c) a spreading layer; d) a bottom support layer including a measuring port in substantial alignment or approximate alignment with the sample aperture. Preferably, the membrane is affixed to the top support layer. Preferably, the membrane is positioned between the top support layer and the bottom support layer. Preferably, the spreading layer is positioned above the top support layer and in substantial or approximate alignment with the sample aperture. Preferably, a fluid applied to the spreading layer, passes through the sample aperture and contacts the membrane.

31 Claims, 7 Drawing Sheets

U.S. PATENT DOCUMENTS

| | | | |
|---|---|---|---|
| 5,563,042 A | 10/1996 | Phillips et al. | 435/4 |
| 5,597,532 A | 1/1997 | Connolly | 435/4 |
| 5,627,075 A | 5/1997 | Bateson | 435/4 |
| D383,550 S | 9/1997 | Larson et al. | 435/4 |
| 5,725,774 A | 3/1998 | Neyer | 435/4 |
| 5,753,452 A | 5/1998 | Smith | 435/4 |
| 5,755,231 A | 5/1998 | Krantz et al. | 435/4 |
| 5,762,871 A | 6/1998 | Neyer | 435/4 |
| 5,770,389 A | 6/1998 | Ching et al. | 435/4 |
| 5,780,304 A | 7/1998 | Matzinger et al. | 435/4 |
| 5,843,691 A | 12/1998 | Douglas et al. | 435/4 |
| 5,843,692 A | 12/1998 | Phillips et al. | 435/4 |
| 5,885,839 A | 3/1999 | Lingane et al. | 435/4 |
| 5,906,916 A | 5/1999 | Wu | 435/4 |
| 5,948,695 A | 9/1999 | Douglas et al. | 435/4 |
| 5,962,215 A | 10/1999 | Douglas et al. | 435/4 |
| 5,968,836 A | 10/1999 | Matzinger et al. | 435/4 |
| 5,972,294 A * | 10/1999 | Smith et al. | 422/58 |
| 6,040,151 A | 3/2000 | Douglas et al. | 435/4 |
| 6,040,195 A | 3/2000 | Carroll et al. | 435/4 |
| 6,087,089 A | 7/2000 | Wu | 435/4 |
| 6,103,141 A | 8/2000 | Incorvia et al. | 435/4 |
| 6,106,780 A | 8/2000 | Douglas et al. | 435/4 |
| 6,121,050 A | 9/2000 | Han | 435/4 |
| 6,162,397 A | 12/2000 | Jurik et al. | 435/4 |
| 6,162,639 A | 12/2000 | Douglas | 435/4 |
| 6,168,957 B1 | 1/2001 | Matzinger et al. | 435/4 |
| 6,268,162 B1 | 7/2001 | Phillips et al. | 435/4 |
| 6,284,550 B1 | 9/2001 | Carroll et al. | 435/4 |
| 6,295,506 B1 | 9/2001 | Heinonen et al. | 435/4 |
| 6,312,888 B1 | 11/2001 | Wong et al. | 435/4 |

\* cited by examiner ical field

The present invention relates generally to the fields of test strip devices and methods of detecting analytes. More specifically, the present invention relates to a test strip for the colormetric detection of glucose in whole blood and methods of use.

BACKGROUND

A variety of test strips for detecting an analyte from a sample are available and described in the literature. Of these, many have applications for the detection of glucose from whole blood. However there are many disadvantages to these devices. Some require a large sample volume to be applied to the test strip, others have a wet through problem and still others lead to contamination of the test strip tray. The present invention addresses these problems and provides related benefits.

SUMMARY

Figure 1A:
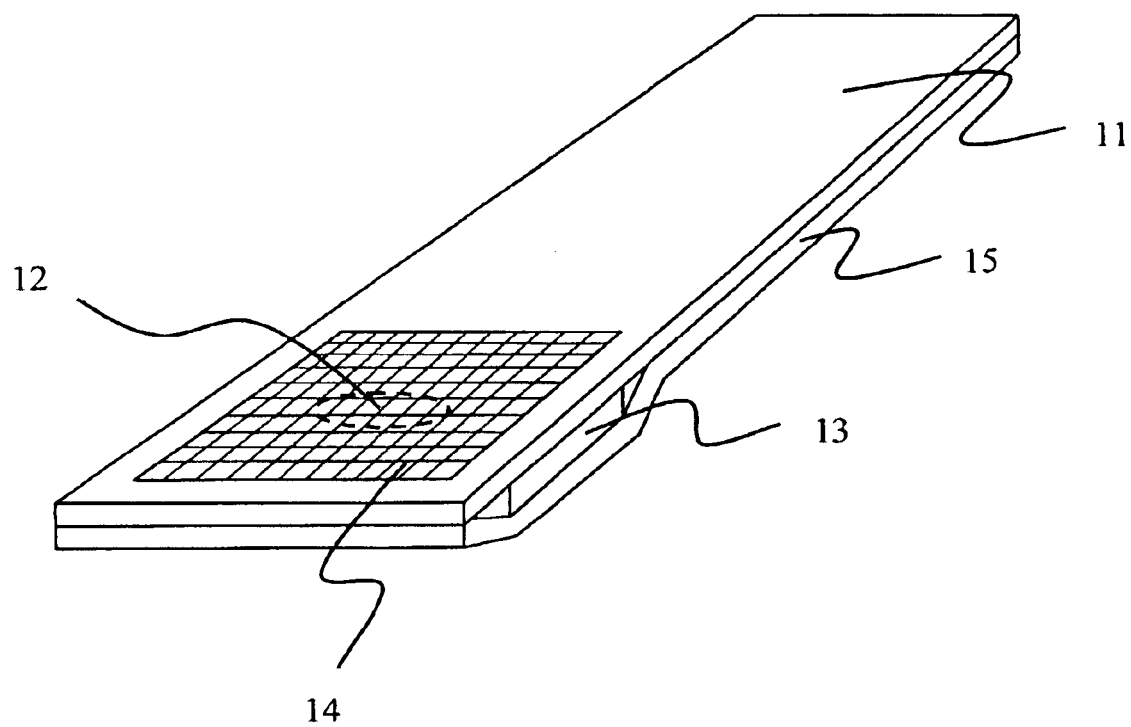
FIGS. 1a and 1b are a perspective and side view of the preferred embodiment of a test strip of the present invention.

The present invention recognizes that traditional test strip design may be improved such that the wet through problem may be reduced and the contamination problem may be reduced by altering the design of a test strip. The present invention provides such a device and methods of use.

A first aspect of the present invention is a reagent test strip that includes: a) a top support layer including a sample aperture; b) a membrane that includes a reagent system for indicating the concentration of a target; c) a spreading layer; and d) a bottom support layer including a measuring port in substantial alignment or approximate alignment with the sample aperture. Preferably, the membrane is affixed to the top support layer. Preferably, the membrane is positioned between the top support layer and the bottom support layer. Preferably, the spreading layer is positioned above the top support layer and in substantial or approximate alignment with the sample aperture. Preferably, a fluid applied to the spreading layer, passes through the sample aperture and contacts the membrane.

A second aspect of the present invention is a method of determining the presence or concentration of a target in a sample that includes the steps of: a) applying a fluid suspected of including a target to the reagent test strip of the present invention; b) detecting the reflectance of the membrane; and c) determining the presence or concentration of the target.

A third aspect of the present invention is a method of determining the concentration of a target in a sample including the steps of: a) detecting a dry strip reading from the reagent test strip of the present invention; b) running a preprogrammed threshold loop instruction; c) detecting a first reflectance measurement; d) running a preprogrammed kinetic loop instruction; and e) determining the presence or concentration of the target. Preferably the threshold loop instruction includes the steps of: detecting a threshold comparison measurement; comparing the threshold comparison measurement to a predetermined threshold value; and repeating the loop until the threshold comparison measurement is less than or equal to the predetermined threshold value. Preferably, a fluid suspected of including a target is applied during the step of running the threshold loop instruction. Preferably the detection loop instruction includes the steps of: detecting a second reflectance measurement; comparing the first reflectance measurement to the second reflectance measurement; ending the loop if the comparison is less than or equal to a predetermined cutoff value; replacing the value of the first reflectance measurement with the value of the second reflectance measurement; and repeating the loop.

A fourth aspect of the present invention is a method of determining the concentration of a target in a sample including the steps of: a) detecting a dry strip reading from the reagent test strip of the present invention; b) running a preprogrammed threshold loop instruction; c) detecting a first reflectance measurement; d) running a preprogrammed kinetic loop instruction; and e) running a consecutive comparison instruction; f) determining the presence or concentration of the target. Preferably, the threshold loop instruction comprises the steps of: detecting a threshold comparison measurement; comparing the threshold comparison measurement to a predetermined threshold value; and repeating the loop until the threshold comparison measurement is less than or equal to the predetermined threshold value. Preferably, a fluid suspected of including a target is applied during the step of running the threshold loop instruction. Preferably, the kinetic loop instruction comprises the steps of: detecting a second reflectance measurement; comparing the first reflectance measurement to the second reflectance measurement; ending the loop if the comparison is less than a predetermined cutoff value; replacing the value of the first reflectance measurement with the value of the second reflectance measurement; and repeating the loop. Preferably, the consecutive comparison instruction comprises the steps of: detecting a third reflectance measurement; comparing the second reflectance measurement to the third reflectance measurement; ending the consecutive comparison instruction if the comparison is less than the predetermined cutoff value; replacing the value of the first reflectance measurement with the value of the third reflectance measurement; and returning to the step of running a kinetic loop instruction.

A fifth aspect of the present invention is a method of determining the concentration of a target in a sample including the steps of: a) detecting a dry strip reading from the reagent test strip of the present invention; b) running a preprogrammed threshold loop instruction; c) beginning a predetermined time point such that a fixed time point may be reached; d) detecting a first reflectance measurement; e) running a preprogrammed kinetic loop instruction; and f) determining the presence or concentration of the target.

Preferably the threshold loop instruction includes the steps of: detecting a threshold comparison measurement; comparing the threshold comparison measurement to a predetermined threshold value; and repeating the loop until the threshold comparison measurement is less than or equal to the predetermined threshold value. Preferably a fluid suspected of including a target is applied during the step of running the threshold loop instruction. Preferably the kinetic loop instruction includes the steps of: detecting a second reflectance measurement; comparing the first reflectance measurement to the second measurement; ending the loop if the second reflectance measurement is less or equal to a predetermined cutoff value or if the fixed time point is reached; replacing the value of the first reflectance measurement with the value of the second reflectance measurement; and repeating the loop.

A sixth aspect of the present invention is a method of determining the concentration of a target in a sample including the steps of: a) detecting a dry strip reading from a reagent test strip of the present invention; b) running a preprogrammed threshold loop instruction; c) beginning a predetermined time point such that a fixed time point may be reached; d) detecting a first reflectance measurement; e) running a preprogrammed kinetic loop instruction; f) running a consecutive comparison instruction; and g) determining the presence or concentration of the target. Preferably the threshold loop instruction comprises the steps of: detecting a threshold comparison measurement; comparing the threshold comparison measurement to a predetermined threshold value; and repeating the loop until the threshold comparison measurement is less than or equal to the predetermined threshold value. Preferably, a fluid suspected of including a target is applied during the step of running the threshold loop instruction. Preferably, the kinetic loop instruction comprises the steps of: detecting a second reflectance measurement; comparing the first reflectance measurement to the second reflectance measurement; ending the loop if the second reflectance measurement is less than or equal to a predetermined cutoff value or if the fixed time point is reached; replacing the value of the first reflectance measurement with the value of the second reflectance measurement; and repeating the loop. Preferably, the consecutive comparison instruction comprises the steps of: detecting a third reflectance measurement; comparing the second reflectance measurement to the third reflectance measurement; ending the consecutive comparison instruction if the comparison is less than or equal to the predetermined cutoff value or if the fixed time point is reached; replacing the value of the first reflectance measurement with the value of the third reflectance measurement; and returning to the step of running a kinetic loop instruction A seventh aspect of the present invention is a method of determining the concentration of a target in a sample including the steps of: a) detecting a dry strip reading from the reagent test strip of the present invention; b) running a preprogrammed threshold loop instruction; c) beginning a predetermined time point such that a fixed time point may be reached; and d) detecting the presence or concentration of a target in a sample when the fixed time point is reached. Preferably the threshold loop instruction includes: detecting a threshold comparison value; comparing the threshold comparison value to a predetermined threshold value; and repeating the loop until the threshold comparison value is less than or equal to the predetermined threshold value. Preferably a fluid suspected of including a target is applied during the step of running the threshold loop instruction.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

The term "wet through" as used herein refers to the tendency of a fluid to migrate around or excessively through a membrane when the membrane is overloaded by fluid. Wet through may cause variations between measurements.

The term "loop instruction" as used herein refers to a set of programmed commands that a computerized device may repeatedly follow until a condition is met. The condition may be part of the loop instruction such that the number of loops performed vary depending on the sample added to the test strip.

The term "threshold value" as used herein refers to an absolute raw value such that a threshold comparison measurement may be detected and directly compared. The threshold value is predetermined and preprogrammed in an apparatus and does not require further calculations such as determining reflectance. Once the threshold comparison measurement is less than or equal to the threshold value the threshold loop instruction ends.

Other technical terms used herein have their ordinary meaning in the art that they are used, as exemplified by a variety of technical dictionaries.

Introduction

The present invention recognizes that traditional test strip design may be improved such that the wet through problem may be reduced, and the contamination problem may be reduced by altering the design of a test strip. The present invention provides such a device and methods of use.

As a non-limiting introduction to the breath of the present invention, the present invention includes several general and useful aspects, including:

1) a reagent test strip that includes: a) a top support layer including a sample aperture; b) a membrane that includes a reagent system for indicating the concentration of a target; c) a spreading layer; d) a bottom support layer including a measuring port in substantial alignment or approximate alignment with the sample aperture;

2) a method of determining the presence or concentration of a target in a sample that includes the steps of: a) applying a fluid suspected of including a target to the reagent test strip of the present invention; b) detecting the reflectance of the membrane; and c) determining the presence or concentration of the target;

3) a method of determining the concentration of a target in a sample including the steps of: a) detecting a dry strip reading from the reagent test strip of the present invention; b) running a preprogrammed threshold loop instruction; c) detecting a first reflectance measurement; d) running a preprogrammed kinetic loop instruction; e) determining the presence or concentration of the target; wherein the threshold loop instruction includes the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction includes the steps of: detecting a second reflectance measurement; comparing the first reflectance measurement to the second reflectance measurement; ending the loop if the comparison is less than or equal to a predetermined cutoff value; replacing the value of the first reflectance measurement with the value of the second reflectance measurement; and repeating the loop;

4) A method of determining the concentration of a target in a sample including the steps of: a) detecting a dry strip reading from the reagent test strip of the present invention; b) running a preprogrammed threshold loop instruction; c) detecting a first reflectance measurement; d) running a preprogrammed kinetic loop instruction; e) running a consecutive comparison instruction; f) determining the presence or concentration of the target; wherein the threshold loop instruction comprises the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction comprises the steps of: detecting a second reflectance measurement; comparing the first reflectance measurement to the second reflectance measurement; ending the loop if the comparison is less than or equal to a predetermined cutoff value; replacing the value of the first reflectance measurement with the value of the second reflectance measurement; and repeating the loop; further wherein the consecutive comparison instruction comprises the steps of: detecting a third reflectance measurement; comparing the second reflectance measurement to the third reflectance measurement; ending the consecutive comparison instruction if the comparison is less than or equal to the predetermined cutoff value; replacing the value of the first reflectance measurement with the value of the third reflectance measurement; and returning to the step of running a kinetic loop instruction;

5) a method of determining the concentration of a target in a sample including the steps of: a) detecting a dry strip reading from the reagent test strip of the present invention; b) running a preprogrammed threshold loop instruction; c) beginning a predetermined time point such that a fixed time point may be reached; d) detecting a first reflectance measurement; f) running a preprogrammed kinetic loop instruction; e) determining the presence or concentration of the target; wherein the threshold loop instruction comprises the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction comprises the steps of: detecting a second reflectance measurement; comparing the first reflectance measurement to the second measurement; ending the loop if the second reflectance measurement is less than or equal to a predetermined cutoff value or if the fixed time point is reached; replacing the value of the first reflectance measurement with the value of the second reflectance measurement; and repeating the loop;

6) a method of determining the concentration of a target in a sample including the steps of: a) detecting a dry strip reading from the reagent test strip of the present invention; b) applying a fluid suspected of including a target to the reagent test strip; c) running a preprogrammed threshold loop instruction; d) beginning a predetermined time point such that a fixed time point may be reached; e) determining the presence or concentration of a target in a sample when the fixed time point is reached; wherein the threshold loop instruction includes: detecting a threshold comparison value; comparing the threshold comparison value to a predetermined threshold value; repeating the loop until the threshold comparison value is less than or equal to the predetermined threshold value; and further wherein a fluid suspected of including a target is applied during the step of running the threshold loop instruction;

7) A method of determining the concentration of a target in a sample including the steps of: a) detecting a dry strip reading from a reagent test strip of the present invention; b) running a preprogrammed threshold loop instruction; c) beginning a predetermined time point such that a fixed time point may be reached; d) detecting a first reflectance measurement; e) running a preprogrammed kinetic loop instruction; f) running a consecutive comparison instruction; g) determining the presence or concentration of the target; wherein the threshold loop instruction comprises the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction comprises the steps of: detecting a second reflectance measurement; comparing the first reflectance measurement to the second reflectance measurement; ending the loop if the second reflectance measurement is less than or equal to a predetermined cutoff value or if the fixed time point is reached; replacing the value of the first reflectance measurement with the value of the second reflectance measurement; and repeating the loop; further wherein the consecutive comparison instruction comprises the steps of: detecting a third reflectance measurement; comparing the second reflectance measurement to the third reflectance measurement; ending the consecutive comparison instruction if the comparison is less than or equal to the predetermined cutoff value or if the fixed time point is reached; replacing the value of the first reflectance measurement with the value of the third reflectance measurement; and returning to the step of running a kinetic loop instruction.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Reagent Test Strip

Figure 1B:
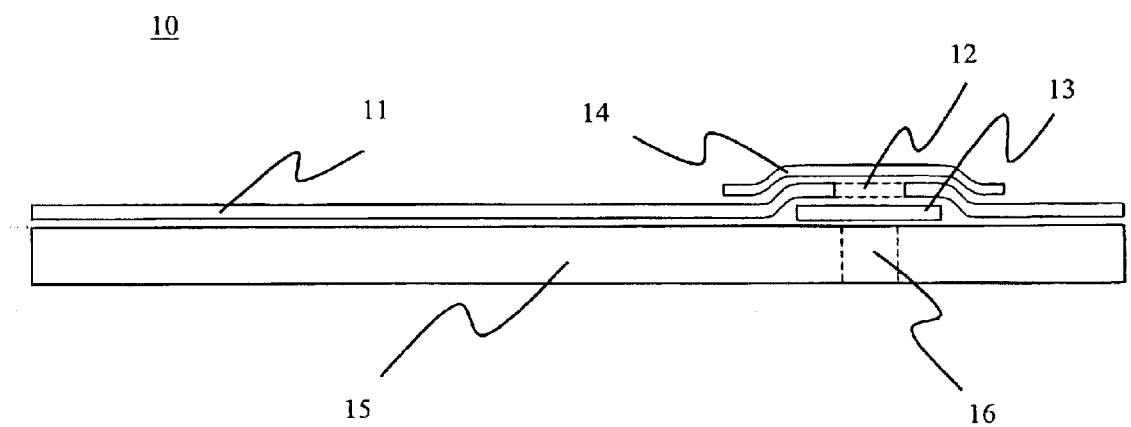

Referring to FIG. 1b, the present invention includes a reagent test strip 10 that includes: a) a top support layer 11 including a sample aperture 12; b) a membrane 13 that includes a reagent system for indicating the concentration of a target; c) a spreading layer 14; d) a bottom support layer 15 including a measuring port 16 in substantial alignment or approximate alignment with the sample aperture 12. Preferably, the membrane 13 is affixed to the top support layer 11. Preferably, the membrane 13 is positioned between the top support layer 11 and the bottom support layer 15. Preferably, the spreading layer 14 is positioned above the top support layer 11 and in substantial or approximate alignment with the sample aperture 12. Preferably, a fluid applied to the spreading layer 14, passes through the sample aperture 12 and contacts the membrane 13.

Each element of the reagent test strip 10 is generally manufactured independently then assembled into the desired configuration. Assembly may involve the individual assembly of a singe test strip 10 or may involve assembling a group of test strips 10 then cutting each test strip 10 into the desired size and shape.

The use of a reagent test strip 10 generally involves inserting the reagent test strip 10 on a test strip tray of a measuring device, detecting a dry strip reading, applying a fluid suspected of including a target to the reagent test strip 10, and detecting the reflectance of the membrane. The present invention may be utilized with a single drop or multiple drops of a fluid.

Top Support Layer

The top support layer 11 may prevent a sample from entering the membrane 13 outside of the region accessible through the sample aperture 12 and may provide a structure enabling the user to grasp the reagent test 10. The top support layer 11 is larger than the sample aperture 12 and is in contact with the membrane 13 outside of the sample aperture 12 thereby eliminating the need for a sink within the test strip 10. Preferably, the top support layer 11 is larger than the membrane.

Figure 2:
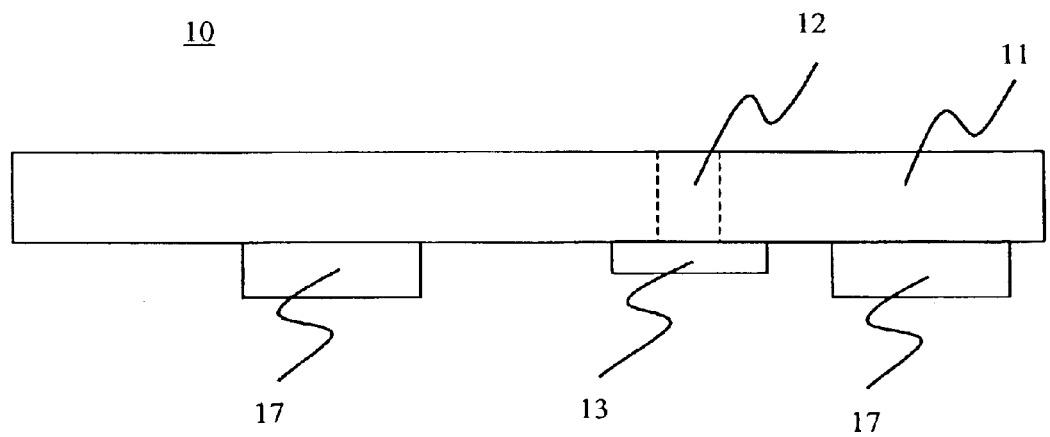
FIG. 2 is a side view of an alternative preferred embodiment of a test strip of the present invention.

The top support layer 11 may be used in combination with a bottom support layer 15 as demonstrated in FIG. 1a or without a bottom support layer 15 as demonstrated in FIG. 2. Referring to FIG. 1a, when used in combination with a bottom support layer 15, the membrane 13 is sandwiched between the top 11 and bottom support layers 15. The top support layer 11 may be affixed to the membrane 13 and to the bottom support layer 15. When the top support layer 11 is used without a bottom support layer 15 as demonstrated in FIG. 2, the membrane 13 is positioned below the top support layer 11 and at least one spacer 17 is affixed to the top support layer 11 such that the membrane 13 is elevated from a test strip tray when the reagent test strip 10 is inserted into a measuring device such as a reflectance meter.

The top support layer 11 is generally manufactured as a sheet, a roll or a card and subdivided into appropriate size portions. The top support layer 11 may be constructed from any material able to substantially exclude the fluid applied to the test strip 10. Some examples are polypropylene, polystyrene, polyesters and polymer plastic. Preferably the dimensions are about five centimeters long by about 6.5 millimeters wide however the dimensions may be different depending on the size of a reflectance meter's test strip tray. The thickness of the top support layer 11 may be from about 0.5 mil to about 30 mil, preferably less than about 5 mil and most preferably from about 2 mil to about 3 mil. However the thickness may vary depending on the desired conformation and rigidity of the test strip 10. For instance, when the top support layer 11 is used in combination with the bottom support layer 15 as demonstrated in FIG. 1b, the bottom support layer 15 may provide the majority of the rigidity allowing a thinner top support layer 11 to be utilized. Alternatively, when the top support layer 11 is not used in combination with the bottom support layer 15 as can be seen by comparing FIG. 1b and FIG. 2, a thicker top support layer 11 may be desired because the top support layer 11 provides the majority of the rigidity.

The top support layer 11 may be affixed to the membrane 13 using a variety of techniques such as by applying an adhesive. Individual adhesives may be desirable depending on the materials chosen for the top support layer 11, membrane 13 and bottom support layer 15. Examples of adhesives that may be utilized with the present invention are acrylic, rubber, ethylene vinyl acetate (EVA) based formulations, hot melt adhesives, and silicon based adhesives.

Referring to FIG. 1b, the sample aperture 12 allows fluid to pass through the top support layer 11 and contact the membrane. The sample aperture 12 should be in substantial alignment or approximate alignment with the measuring port 16 such that a target migrates in a substantially vertical path through the sample aperture 12. The fluid may migrate through the sample aperture 12 by gravitational forces or by capillary forces.

Bottom Support Layer

The bottom support layer 15 may prevent or reduce contact between the membrane 13 and a test strip tray of a measuring device, may add rigidity to the test strip 10 and may provide a structure enabling the user to grasp the reagent test strip 10. Referring to FIG. 1b, the bottom support layer 15 includes a measuring port 16 in substantial alignment or approximate alignment with the sample aperture 12 such that a measuring device such as a reflectance meter may measure a surface of the membrane 13.

The bottom support layer 15 may be constructed from any material able to substantially exclude the fluid applied to the test strip 10 such that the sample does not leak through the bottom support layer 15 and contact the user or the test strip tray. Moreover, it may be desirable to construct the bottom support layer 15 from a material sufficiently rigid such that the test strip 10 may be inserted into a measuring apparatus without undue bending or kinking. Some examples of appropriate materials are polypropylene, polystyrene, polyesters, and polymer plastic. The bottom support layer 15 is generally manufactured as a sheet, a roll, or a card then subdivided into appropriate size portions. Preferably the dimensions are about five centimeters long by about 6.5 millimeters wide. The thickness may be from about 1 mil to about 30 mil. The bottom support layer 15 may be affixed such as by adhesive to the membrane 13 or to the top support layer 11 or both. Suitable adhesives are acrylic, rubber, ethylene vinyl acetate (EVA) based formulations, hot melt adhesives and silicon based adhesives.

The measuring port 16 provides a region whereby a measuring device such as a reflectance meter is able to detect the reflectance from the surface of the membrane 13. The measuring port 16 should be sufficiently large that the bottom support layer 15 does not interfere with the detection of a reflectance meter when the test strip 10 is correctly inserted into a reflectance meter test strip tray. Preferably, the measuring port 16 is an aperture.

Spreading Layer

The spreading layer 14 distributes the sample uniformly across the sample aperture 12 such that the sample may migrate uniformly towards the membrane. Referring to FIG. 1b, the spreading layer 14 is positioned above and in substantial alignment or approximate alignment with the sample aperture 12. Generally the spreading layer 14 is adhesively affixed to the top support layer 11. The pores should be sufficiently large to allow the target to flow through the spreading layer 14. Preferably, the spreading layer 14 is constructed of a material that requires minimum sample volume, absorbs fluids quickly, and distributes fluids uniformly to the membrane 13 through the sample aperture 12. Some examples of suitable materials for the spreading layer 14 are nylon, paper, glass fibers, polymer fibers, sintered plastics, woven fabrics, non-woven fabrics, and membranes.

Membrane

A sample migrates through the spreading layer 14, the sample aperture 12, and contacts the membrane 13. As the sample is absorbed into the membrane 13, the pore size prevents larger particulates from passing through the membrane 13. The remaining sample continues to migrate through the membrane 13 and contacts the reagent system where the signal is generated. The signal is detected from the surface of the membrane 13 opposite the sample aperture 12.

The pore size of the membrane 13 determines the degree of size exclusion and may vary depending on the target of interest and the compounds the user wishes to exclude. Generally when utilizing the present invention with biological samples such as blood and performing an optical glucose detection assay, the pore size should be from about 0.1 um to about 15 um. The membrane 13 may comprise a uniform pore size or variable pore sizes. When the pore size is variable, pores may be configured in either a symmetric gradient or an asymmetric gradient configuration. Some examples of materials suitable for constructing a membrane 13 are polysulfone, polyethersulfone, nitrocellulose, and nylon. Polyethersulfone membranes are particularly well at reducing red blood cell lyses.

The membrane 13 may be positively charged, negatively charged or may have no charge. The membrane 13 charge may be the net charge after impregnating the membrane 13 with a reagent buffer. For instance, impregnating a neutrally charged membrane 13 with an acidic buffer may result in a net positive charge. When detecting the presence of glucose in whole blood, preferably the membrane 13 is hydrophilic and either positively, negatively, or neutrally charged.

Reagent System

The reagent system functions as an indicator in the direct or indirect presence of a target such that the target's presence in the sample may be detected. A reagent system must therefore be able to react with the target directly or indirectly and must yield a detectable signal. Typically, the reagent system comprises an enzyme system covalently or non-covalently bound to the membrane. Preferably, the enzyme system selectively catalyzes a primary reation with the analyte of interest. A product of the primary reaction may be a dye or chromophore which undergoes a change in color that is detectable on the surface of the membrane 13 opposite the sample aperture 12. Alternatively, the product of the primary reaction may be an intermediate which undergoes another reaction, preferably also enzyme catalyzed, and participates in a secondary reaction which, directly or indirectly, causes a dye or chromophore to undergo a change in color which is detectable on the surface of the membrane 13 opposite the sample aperture 12. The signal is then detected visually or by a measuring devices such as a reflectance meter, and the presence or concentration of the target may be determined.

An enzyme system comprises at least one enzyme. In some instances two or more enzymes may be used in combination with one another. In addition, the reagent system may comprise a substrate capable of forming a chromophore. When this configuration is used, the chromophore is indicative of the presence or concentration of the target.

When the target is glucose, a useful reagent system comprises glucose oxidase and horseradish peroxidase. Glucose oxidase reacts with glucose and oxygen to produce gluconolactone and hydrogen peroxide. Hydrogen peroxide in the presence of a peroxidase such as horseradish peroxidase oxidizes a dye or chromophore and produces a detectable signal. In this configuration, the reflectance may be measured from about 500 m to about 800 nm, preferably from about 600 nm to about 700 nm, most preferably about 660 nm. Examples of substrates that may be utilized with the present invention are o-dianisidine, o-toluidine, o-tolidine, 2,2'-Azinodi-(3-ethylbenz-thiazoline sulphonic acid-(6)), 3-methyl-2-benzothiazolinone hydrazone plus N,N-dimethylaniline, phenol plus 4-aminophenazone, sulfonated 2,4-dichlorophenol plus 4-amino-phenazone, 3-methyl-2-benxothiazoline hydrazone plus 3-(dimethylamino)benzoic acid, 2-methoxy-4-allyl phenol, 4-aminoantipyrine-dimethylaniline, MTBH-DMAB dye couple (3-methyl-2-benzothiazolinone hydrazone hydrochloride and 3-dimethylaminobenzoic acid), AAP-CTA dye couple (4-aminoantipyrene and chromotropic acid), 3-methyl-2-benzothiazoline hydrazone in free form or in acid form (MTBH) and 8-anilino-1-napthalenesulfonate in acid or free form (ANS), 4-aminoantipyrene (AAP) and chromotropic acid, AAP and 8-anilino-1-napthalensulfonate (ANS), AAP and N-ethyl-N-(2 hydroxy-3-sulfopropyl)-m-toludine (TOOS), MTBH combined with its formaldehyde azine, leuco methylene blue, BISMAP, AAP and MAPS, AAP and N-ethyl-N-(2-hydroxy-3-sulfopropyl)-3,5-dimethylanine, sodium salt, monohydrate (MAOS), SMBTH and MAOS, AAP and 8-anilino-1-natphthalenesulfonate (ANS), MTBH combined with its formaldehyde azine, 3,3,5,5-tertramethylbenzidine (TMB), 4-aminoantipyrine. In addition the following substrates may also be utilized with the present invention. SMBTH and ALPS, MBTH and ALPS, AAP and DAPS, AAP and DAOS, MBTH and DMAB, BISMAP, and combinations thereof.

Target

The present invention is useful in detecting a variety of targets from a variety of samples. Preferably the target is glucose and the sample is whole blood. However, the present invention may be adapted for detecting the concentration or presence of a variety of targets by modifying the membrane 13 to include a reagent system that can detect the desired target. Generally the target is a biological moiety or a chemical moiety. The target may be a protein or a nucleic acid.

Wet Through

The present invention provides improvements relative to currently available technologies. Three problems are common with conventional test strips. First, test strips that do not have a top support layer often have a wet through problem. Secondly, test strips that do not have a bottom support layer and do not have at least one spacer may have contamination problems associated with wet through. Third, test strips that have a spreading layer positioned between two support layers require additional material such as an absorbent sink to capture excess fluid. Referring to FIG. 1a, the present invention reduces the wet through problem by utilizing a top support layer 11 with a sample aperture 12 such that the membrane 13 is in contact with the top support layer 11. The present invention solves the contamination problem by incorporating either a bottom support layer 15 with a measuring port 16 as demonstrated in FIG. 1b or by incorporating spacers 17 as demonstrated in FIG. 2.

A wet through problem occurs when excess sample is added to a membrane. The excess sample overloads the membrane and may leak around or through the membrane. A conventional solution to address this problem is the addition of an absorbent sink, see WO 92/15863. However, the absorbent sink configuration does not function well when small sample volumes are applied. A large region houses both the membrane and the sink requiring the user to apply a greater volume of sample than a configuration with a membrane affixed to a top support layer. Importantly, one aim in the design of test strips is to minimize sample volume for the user. Therefore referring to FIG. 1a, present invention significantly reduces the wet through problem by contacting the membrane 13 to the top support layer 11 such that the membrane 13 is in substantial alignment or approximate alignment with the sample aperture 12.

A problem inherent in test strips that do not have a bottom support layer is contamination of the test device, another test strip, or of another user. Test strips are generally placed in reflectance meters. When a traditional test strip absent a bottom support layer such as the device disclosed in U.S. Pat. No. 5,753,452 is inserted into the meter, the membrane may contact the measuring device. This may lead to a smearing of the reagent system or fluid containing the target on the test meter and may require the user to frequently clean the test meter. Additionally when a sample is a biological fluid such as whole blood, a portion of the sample may smear on the test strip tray and may come in contact with another user. The present invention overcomes these problems by the presence of a bottom support layer 15 as demonstrated in FIG. 1b or spacers 17 as demonstrated in FIG. 2. The present invention suspends the membrane 13 from the meter thus preventing contact between the membrane 13 and the meter.

Optional Spacer

Referring to FIG. 2 in another aspect of the present invention, a reagent test strip 10 is disclosed including a) a top support layer 11 including a sample aperture 12; b) a membrane 13 including a reagent system for indicating the presence or concentration of a target; c) at least one spacer 17 able to reduce contact between the membrane 13 and a surface; and wherein the membrane 13 is positioned below the top support layer 11 and in substantial alignment or approximate alignment with the sample aperture 12.

A spacer 17 functions to elevate the membrane 13 from a surface such as a test strip tray of a measuring device. The spacer may be any constructed from any material able to withstand the weight of the test strip 10. The size and number of the spacers 17 may be dependent on the configuration of the test strip tray and should elevate the membrane 13 from the test strip tray when inserted into the measuring device. The spacer 17 is generally adhesively affixed to the top support layer 11 on the same surface as the membrane. Some examples of appropriate materials are polypropylene, polystyrene, polyesters, polymer plastic, and paper.

II Method for Determining Presence or Concentration of a Target Using the Test Strip The present invention also includes a method of determining the presence or concentration of a target in a sample that includes the steps of: a) applying a fluid suspected of including a target to the reagent test strip 10 of the present invention; b) detecting the reflectance of the membrane; and c) determining the presence or concentration of the target.

A fluid suspected of including a target may be applied using a variety of techniques such as by directly contacting the fluid to the test strip 10 or by using a dispensing device such as a capillary tube. Directly applying a fluid to the test strip 10 may be preferred by those that monitor target concentration outside of the laboratory such as routine glucose testing in diabetic patients. Diabetic patients generally require multiple measurements of plasma glucose during the day and prick a portion of the body to draw a small amount of whole blood.

The presence or absence of a target is determined by the change in reflectance of the membrane 13. The reagent system produces a chromophore that exhibits a color change upon direct or indirect exposure to the target. The reflectance may be detected visually by observing a color change or may be detected using a measuring device such as a reflectance meter. When visually inspecting a color change, a color chart may be provided as a series of standards. The preferred measuring device is a reflectance meter. A reflectance meter has the advantage of higher sensitivity and accuracy. Concentration may be determined directly from the reflectance value. Alternatively, the reflectance may be converted to a K/S value then converted to concentration. The relationship between the K/S value and reflectance has as described in D. B. Judd and G. Wyszeki, *Color in Business, Science and Industry* (John Wiley & Sons, NY (1975)), which is herein incorporated by reference.

Figure 3:
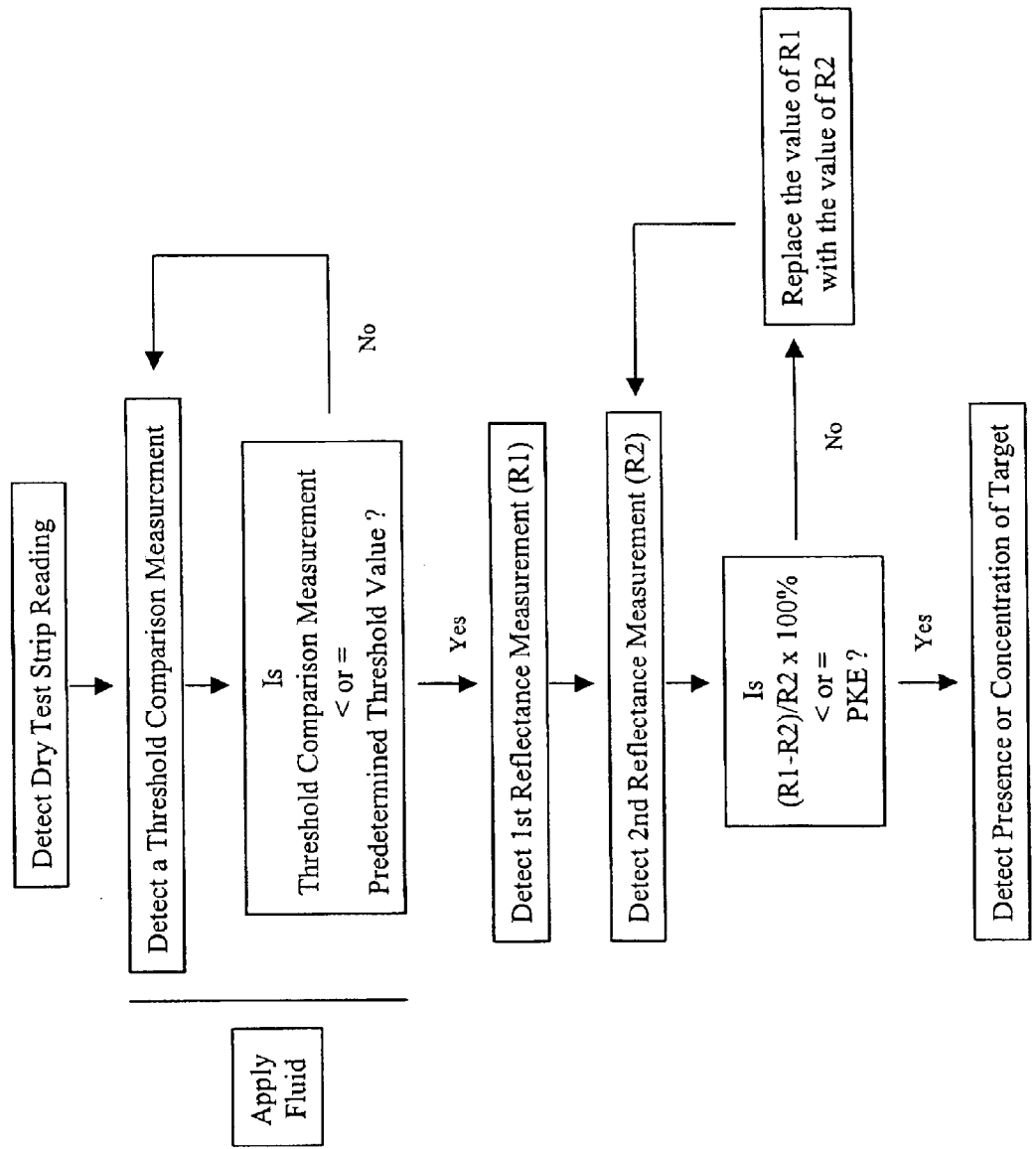
FIG. 3 is a block diagram of a preferred embodiment of a method for detecting the presence or concentration of a target using kinetic endpoint measurements.

III Method for Detecting the Presence or Concentration of a Target Using Kinetic Endpoint Measurements The present invention also provides a method of determining the presence or concentration of a target that once the reaction between the target and the reagent system is complete or near completion. The assay is complete or near complete when the difference between two reflectance values is equal to or less than a predetermined kinetic endpoint. This method may be utilized with any reagent test strip that undergoes a measurable change in light scatter until a kinetic endpoint is reached. Referring to FIG. 3, the method of determining the concentration of a target in a sample includes the steps of: a) detecting a dry strip reading from the reagent test strip of the present invention; running a preprogrammed threshold loop instruction; c) detecting a first reflectance measurement; d) running a preprogrammed kinetic loop instruction; e) determining the presence or concentration of the target; wherein the threshold loop instruction includes the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the detection loop instruction includes the steps of: detecting a second reflectance measurement; comparing the first reflectance measurement to the second reflectance measurement; ending the loop if the comparison is less than or equal to a predetermined kinetic endpoint; replacing the value of the first reflectance measurement with the value of the second reflectance measurement; and repeating the loop.

A dry strip reading functions as a reference value allowing the first and/or second reflectance measurement to be normalized. A fluid suspected of including the target is applied to the test strip 10 and gravity or capillary force causes the target to migrate through the membrane. Once the surface of the membrane 13 opposite the sample aperture 12 is moistened, the light scatter is reduced. When the detected value drops below a predetermined threshold value, two measurements may be taken at predetermined time intervals. These measurements are the first reflectance measurement and the second reflectance measurement respectively. The second reflectance measurement is compared to the first reflectance measurement. When the comparison is less than or about equal to the predetermined kinetic endpoint, the reaction is complete or near completed and the concentration of the target may be determined. The predetermined kinetic endpoint may be from about 0.2% to about 5% and preferably from about 0.5% to about 1%. Generally the concentration is determined using the second reflectance measurement, however the first reflectance measurement or a new reflectance measurement may also be used. Alternatively, if the comparison value is greater than the predetermined kinetic endpoint, the value representing the first reflectance measurement may be replaced with the value of the second reflectance measurement and a new second reflectance measurement may be determined and compared to the newly replaced first reflectance measurement. As an alternative to replacing the first reflectance measurement with the second reflectance measurement, the present invention encompasses a loop instruction whereby a third reflectance measurement may be determined and compared to the second reflectance measurement. The present invention also encompasses comparing at least two sets of reflectance measurements such that both sets must be equal to or less than the predetermined kinetic endpoint.

The method of determining whether the kinetic endpoint is reached may be performed by calculating the change in reflectance measurements and comparing the result to a predetermined value. For instance, if R1 represents a first reflectance measurement, R2 represents a second reflectance measurement, and 1% represents the predetermined kinetic endpoint (PKE), the comparison (C) may be performed by the following formula: $C=((R1-R2)/R2)\times 100\%$. If C is less than or equal to PKE, in this example 1%, the concentration of the target is calculated. Otherwise the value of R2 becomes R1 and a new R2 is determined and compared to the new R1. The cycle continues until the comparison, C, is less than or equal to the predetermined kinetic endpoint, PKE. The present invention recognizes that the predetermined kinetic endpoint and comparison values are not limited to a percentage but may reflect a variety of units.

Figure 4:
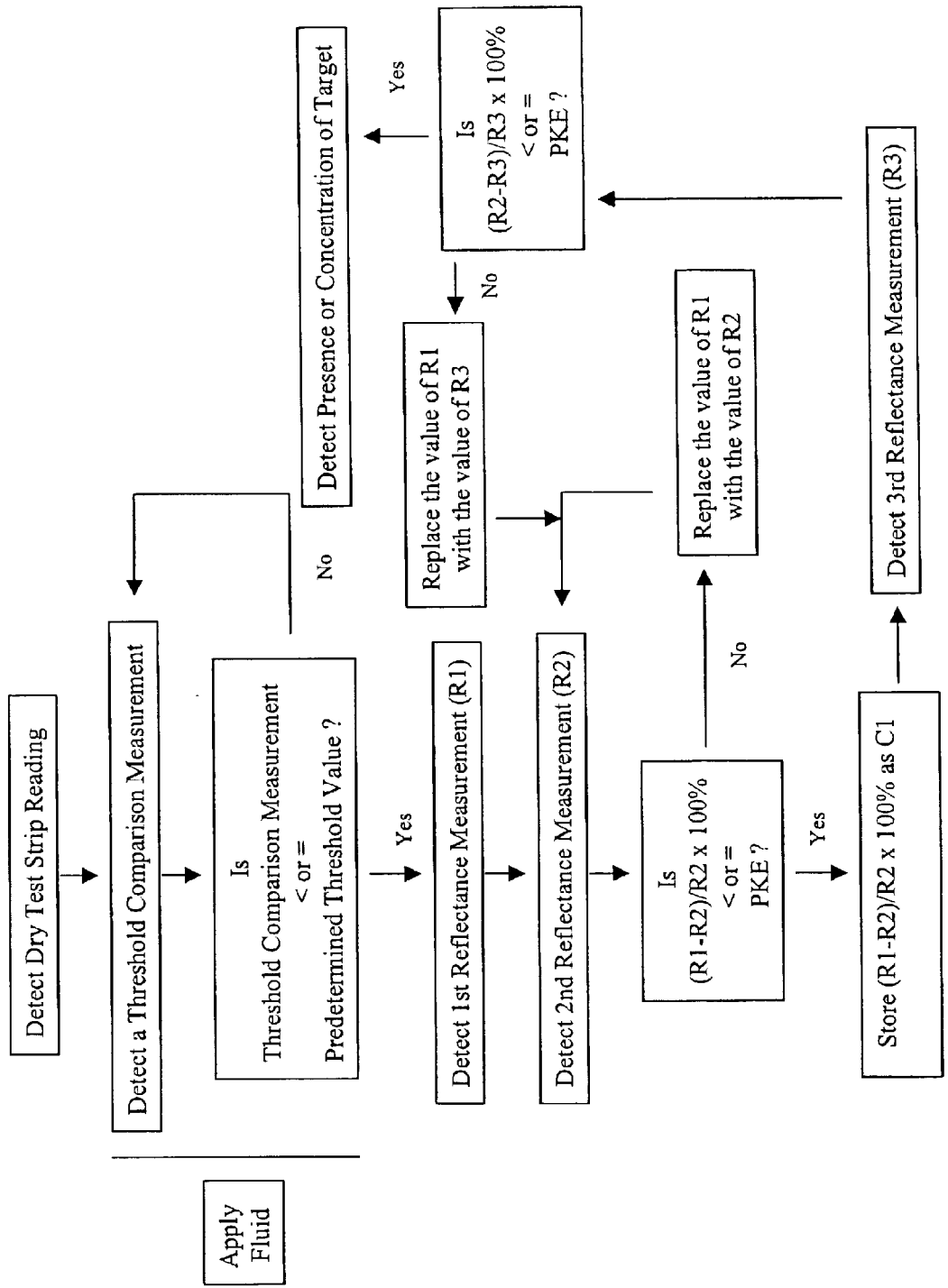
FIG. 4 is a block diagram of another preferred embodiment of a method for detecting the presence or concentration of a target using kinetic endpoint measurements.

Alternatively a comparison may be desired between at least two sets of reflectance values such that the both comparisons are less than or equal to the predetermined kinetic endpoint. Multiple sets of reflectance values may be utilized in this manner. Referring to FIG. 4, a method of determining the concentration of a target in a sample is disclosed including the steps of: a) detecting a dry strip reading from the reagent test strip of the present invention; b) running a preprogrammed threshold loop instruction; c) detecting a first reflectance measurement; d) running a preprogrammed kinetic loop instruction; e) running a consecutive comparison instruction; f) determining the presence or concentration of the target; wherein the threshold loop instruction comprises the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction comprises the steps of: detecting a second reflectance measurement; comparing the first reflectance measurement to the second reflectance measurement; ending the loop if the comparison is less than or equal to a predetermined cutoff value; replacing the value of the first reflectance measurement with the value of the second reflectance measurement; and repeating the loop; further wherein the consecutive comparison instruction comprises the steps of: detecting a third reflectance measurement; comparing the second reflectance measurement to the third reflectance measurement; ending the consecutive comparison instruction if the comparison is less than or equal to the predetermined cutoff value; replacing the value of the first reflectance measurement with the value of the second reflectance measurement; and returning to the step of running a kinetic loop instruction. For example in addition to the equation above, it may be desirable to obtain third reflectance and fourth reflectance values, R3 and R4. In this instance $C1=((R1-R2)/R2)\times 100\%$ and $C2=((R4-R3)/R4)\times 100\%$. The concentration may be determined once C1 and C2 are less than or equal to PKE. Referring to FIG. 4, the present invention also encompasses the condition where $C1=((R1-R2)/R2)\times 100\%$ and $C2=((R3-R2)/R3)\times 100\%$.

As an alternative to calculating concentration directly from reflectance, the K/S ratio of the membrane 13 may also be utilized with the present invention. Kubelka and Munk derived the K/S ratio and has been described in D. B. Judd and G. Wyszeki, *Color in Business, Science and Industry* (John Wiley & Sons, NY (1975)), which is herein incorporated by reference. The K/S ratio is related to the reflectance by $K/S=(1-R)^2/2R$.

IV Method of Detecting a Target Using a Fixed Time Point and Kinetic Endpoint Measurements A hybrid method including a fixed time point method and kinetic endpoint method may also be utilized to determine the presence or concentration of a target in a sample. In this aspect, the kinetic method operates as previously described however in addition, a fixed time point is also calculated. The fixed time point is the end of a predetermined time point that begins once the threshold value is reached or nearly reached. The method continues so long as either the comparison between the first reflectance reading and the second reflectance reading do not meet the predetermined kinetic endpoint or the fixed time point is reached, whichever is reached first. This method may be utilized with any reagent test strip that undergoes a measurable change in light scatter until a kinetic endpoint is reached.

Figure 5:
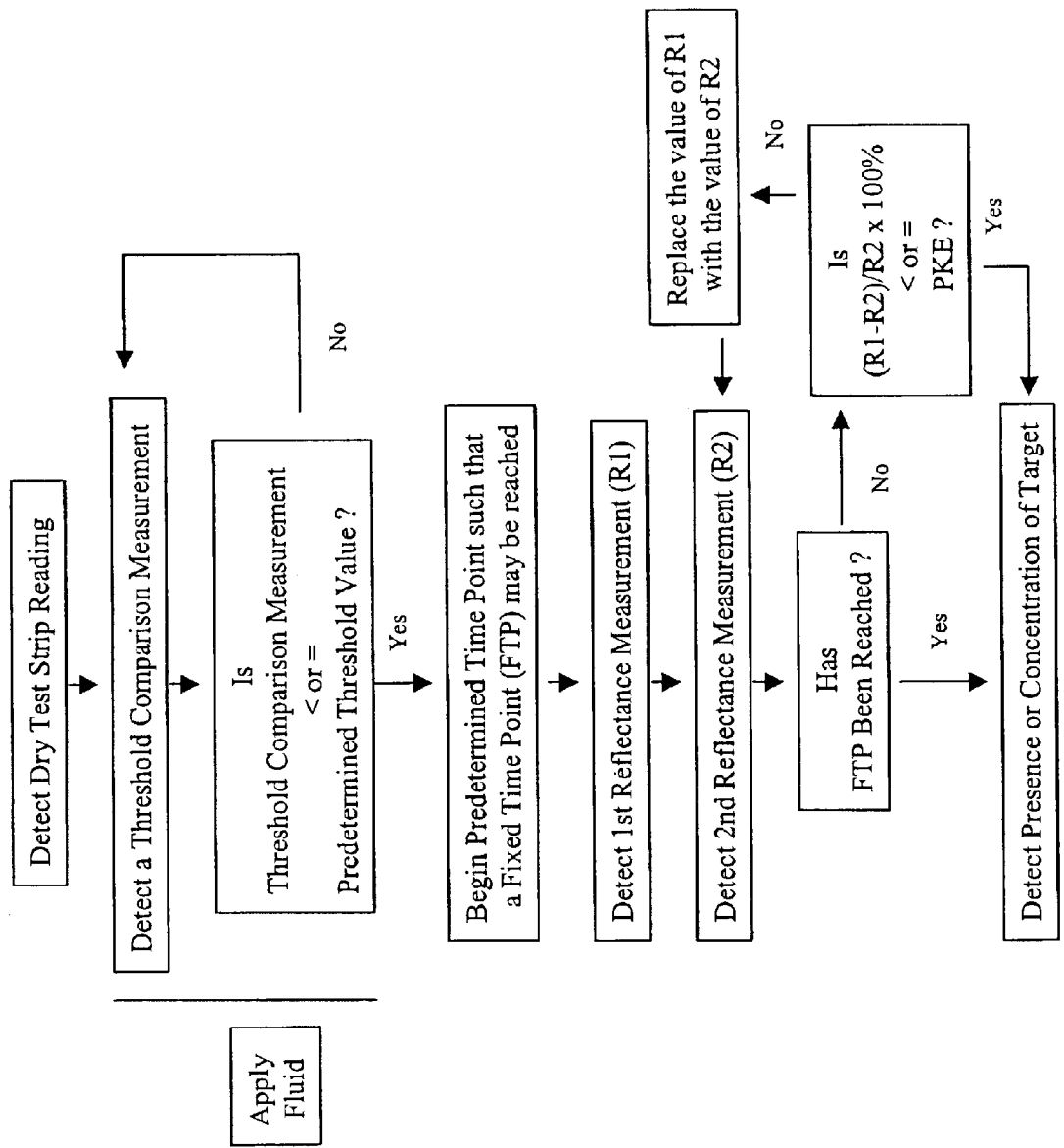
FIG. 5 is a block diagram of a preferred embodiment of a method for detecting the presence or concentration of a target using a fixed time point and kinetic measurements.

Referring to FIG. 5, the present invention includes a method of determining the concentration of a target in a sample including the steps of: a) detecting a dry strip reading from the reagent test strip of the present invention; b) applying a fluid suspected of including a target to the reagent test strip; c) running a preprogrammed threshold loop instruction; d) beginning a predetermined time point such that a fixed time point may be reached; e) detecting a first reflectance measurement; and f) running a preprogrammed kinetic loop instruction; g) determining the presence or concentration of the target. Preferably the threshold loop instruction comprises the steps of: detecting a threshold comparison measurement; comparing the threshold comparison measurement to a predetermined threshold value; and repeating the loop until the threshold comparison measurement is less than or equal to the predetermined threshold value. Preferably the kinetic loop instruction comprises the steps of: detecting a second reflectance measurement; comparing the first reflectance measurement to the second measurement; ending the loop if the second reflectance measurement is less or equal to a predetermined cutoff value or if the fixed time point is reached; replacing the value of the first reflectance measurement with the value of the second reflectance measurement; and repeating the loop.

Figure 6:
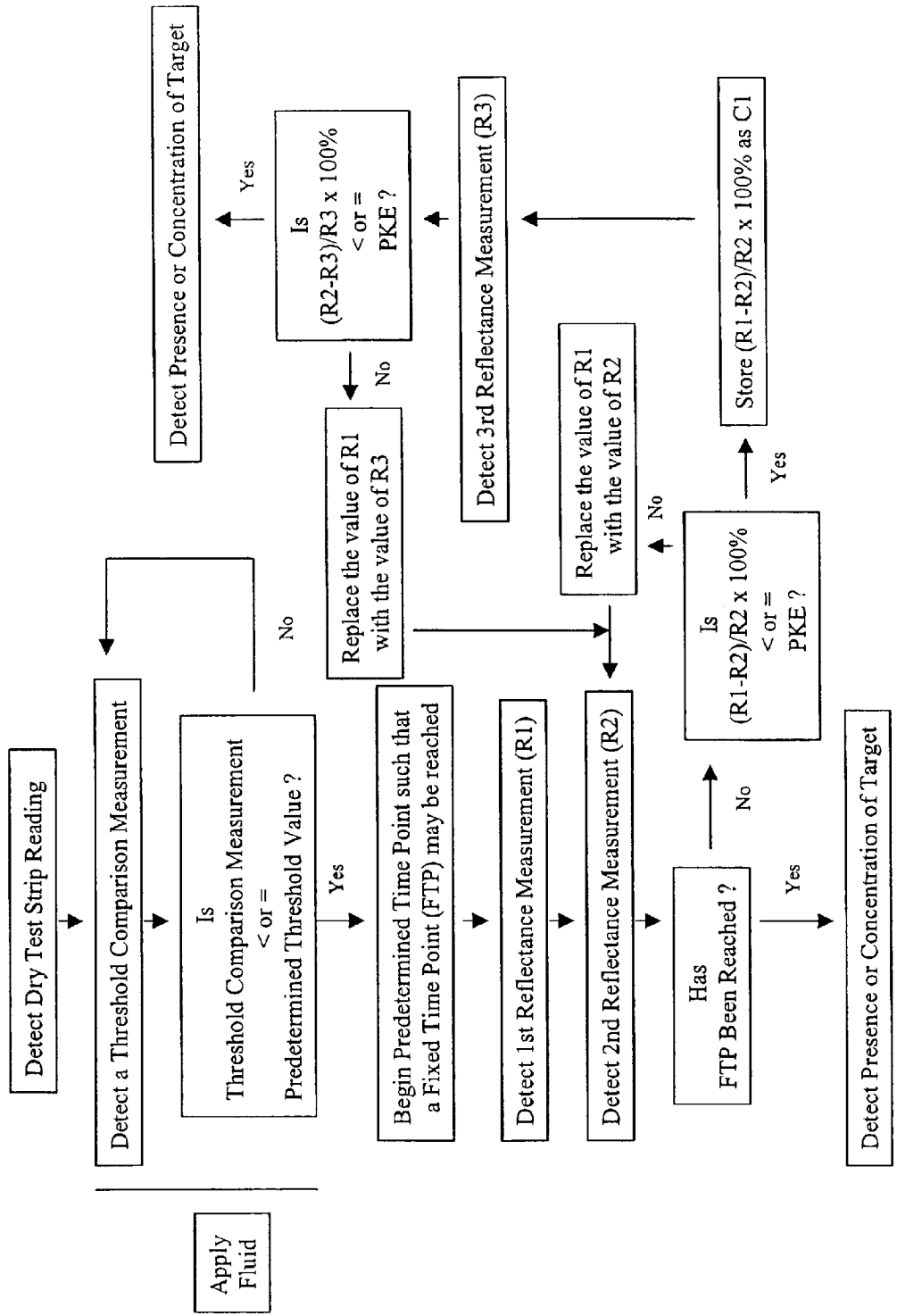
FIG. 6 is a block diagram of another preferred embodiment of a method for detecting the presence or concentration of a target using a fixed time point and kinetic measurements.

Referring to FIG. 6, the present invention also discloses a method of determining the concentration of a target in a sample including the steps of: a) detecting a dry strip reading from a reagent test strip of the present invention; b) running a preprogrammed threshold loop instruction; c) beginning a predetermined time point such that a fixed time point may be reached; d) detecting a first reflectance measurement; e) running a preprogrammed kinetic loop instruction; f) running a consecutive comparison instruction; g) determining the presence or concentration of the target; wherein the threshold loop instruction comprises the steps of: detecting a threshold comparison measurement; comparing the threshold comparison measurement to a predetermined threshold value; repeating the loop until the threshold comparison measurement is less than or equal to the predetermined threshold value; further wherein a fluid suspected of including a target is applied during the step of running the threshold loop instruction; further wherein the kinetic loop instruction comprises the steps of: detecting a second reflectance measurement; comparing the first reflectance measurement to the second reflectance measurement; ending the loop if the second reflectance measurement is less than or equal to a predetermined cutoff value or if the fixed time point is reached; replacing the value of the first reflectance measurement with the value of the second reflectance measurement; and repeating the loop; further wherein the consecutive comparison instruction comprises the steps of: detecting a third reflectance measurement; comparing the second reflectance measurement to the third reflectance measurement; ending the consecutive comparison instruction if the comparison is less than or equal to the predetermined cutoff value or if the fixed time point is reached; replacing the value of the first reflectance measurement with the value of the second reflectance measurement; and returning to the step of running a kinetic loop instruction.

V. Method of Detecting a Target Using a Fixed Time Point

The present invention also provides a method of determining the presence or concentration of a target once a fixed time point is reached. The fixed time point begins once the threshold comparison measurement is less than or equal to the predetermined threshold value. The present invention provides for a method of determining the concentration of a target in a sample including the steps of: a) detecting a dry strip reading from the reagent test strip 10 of the present invention; b) applying a fluid suspected of including a target to the reagent test strip 10; c) running a preprogrammed threshold loop instruction; d) beginning a predetermined time point such that a fixed time point may be reached; and e) determining the presence or concentration of a target in a sample when the fixed time point is reached. Preferably the threshold loop instruction includes: detecting a threshold comparison value; comparing the threshold comparison value to a predetermined threshold value; repeating the loop until the threshold comparison value is less than or equal to the predetermined threshold value.

EXAMPLES

Example I

Demonstration of Decreased Wet Through Problem with a Test Strip of the Present Invention The following example illustrates the ability of a test strip 10 of the present invention to reduce the wet through problem associated with alternative test strip 10 configurations.

The membranes 13 in each of the following configurations were prepared in the same manner. The membrane 13, Biodyne A nylon membrane 13 having a 0.65 um pore size (Pall Corp., Port Washington, N.Y.), was impregnated with a glucose oxidase/horseradish peroxidase exyme system (Toyobo Inc., Tokyo, Japan) and AAP (4-aminoantipyrene, Sigma, St. Louis, Mo.)/MAOS (N-ethyl-N-(2-hydroxy-3-sulfopropyl)-3,5-dimethylanine, sodium salt, monohydrate, Dojindo Laboratories, Dumamoto, Japan) dye system.

Configuration A is one aspect of the present invention. Configuration A includes a membrane 13 affixed to the top support layer 11 and positioned above the bottom support layer 15 allowing a reflectance meter to measure light scatter through the measuring port 16. A hydrophilic, woven, polyester, mesh spreading layer 14 (SaatiTech, Inc., Veniano, Italy) is positioned above the top support layer 11 in substantial and approximate alignment with the sample aperture 12 of the top support layer 11.

Alternative configurations for comparison are as follows. Configuration B includes a membrane 13 and a hydrophilic, woven, polyester, mesh spreading layer 14 (SaatiTech, Inc., Veniano, Italy) sandwiched between the top support layer 11 and the bottom support layer 15 such that the spreading layer 14 is positioned between the top support layer 11 and the membrane 13. Configuration C includes a membrane 13 affixed to the base support layer such that the sample is applied directly to the membrane 13.

Whole blood samples with adjusted hematocrit of 42% and treated with sodium heparin as an anticoagulant, were prepared by spiking the sample with a concentrated glucose solution. Whole blood samples having glucose at a concentration of about 100, 250 and 450 mg/dL were prepared. The final glucose concentrations were verified by a YSI 2300 STAT-PLUS Glucose Analyzer (Yellow Springs Instruments Icn., Yellow Springs, Ohio).

Samples of 5, 10, 20 and 30 uL were applied to 10 strips of each configuration. Each sample was added to the test strip 10 once the test strip 10 was inserted into a reflectance meter and the reflectance was measured at 660 nm. Reflectance readings were converted to glucose concentration values based on a calibration curve, averaged within each test group, normalized to the 5 uL test group (Table 1) and the coefficient of variation (CV) was determined (Table 2). The test strips 10 were then visually observed for wet through (Table 3).

TABLE 1

| Glucose mg/dL (by YSI) | | 5 uL (% Difference vs. 5 uL) | 10 uL (% Difference vs. 5 uL) | 20 uL (% Difference vs. 5 uL) | 30 uL (% Difference vs. 5 uL) |
|---|---|---|---|---|---|
| 104 | Configuration A | 0 | +4.4 | +5.1 | +2.8 |
| 104 | Configuration B | 0 | +8.0 | +11.3 | +15.0 |
| 104 | Configuration C | 0 | +1.2 | +6.5 | +10.3 |
| 246 | Configuration A | 0 | −2.1 | −5.0 | −4.0 |
| 246 | Configuration B | 0 | +2.1 | +20.4 | +39.9 |
| 246 | Configuration C | 0 | −2.6 | +3.8 | +20.7 |

TABLE 1-continued

| Glucose mg/dL (by YSI) | | 5 uL (% Difference vs. 5 uL) | 10 uL (% Difference vs. 5 uL) | 20 uL (% Difference vs. 5 uL) | 30 uL (% Difference vs. 5 uL) |
|---|---|---|---|---|---|
| 467 | Configuration A | 0 | +1.8 | −8.9 | −9.7 |
| 467 | Configuration B | 0 | +23.8 | +54.9 | +147.1 |
| 467 | Configuration C | 0 | +2.9 | +15.3 | +38.7 |

TABLE 2

| Glucose mg/dL (by YSI) | | 5 uL (% CV) | 10 uL (% CV) | 20 uL (% CV) | 30 uL (% CV) |
|---|---|---|---|---|---|
| 104 | Configuration A | 5.5 | 3.4 | 5.7 | 5.2 |
| 104 | Configuration B | 3.3 | 4.2 | 2.5 | 2.7 |
| 104 | Configuration C | 3.0 | 2.1 | 3.5 | 3.7 |
| 246 | Configuration A | 3.3 | 3.2 | 4.7 | 3.4 |
| 246 | Configuration B | 3.1 | 4.1 | 3.5 | 3.8 |
| 246 | Configuration C | 1.8 | 1.9 | 6.6 | 10.1 |
| 467 | Configuration A | 4.6 | 3.5 | 4.4 | 5.6 |
| 467 | Configuration B | 5.3 | 4.1 | 4.2 | 9.0 |
| 467 | Configuration C | 3.7 | 3.3 | 6.4 | 14.8 |

TABLE 3

| Glucose mg/dL (by YSI) | | 5 uL Wet Through | 10 uL Wet Through | 20 uL Wet Through | 30 uL Wet Through |
|---|---|---|---|---|---|
| 104 | Configuration A | No | No | No | No |
| 104 | Configuration B | No | Yes | Yes | Yes |
| 104 | Configuration C | No | No | Yes | Yes |
| 246 | Configuration A | No | No | No | No |
| 246 | Configuration B | No | Yes | Yes | Yes |
| 246 | Configuration C | No | No | Yes | Yes |
| 467 | Configuration A | No | No | No | No |
| 467 | Configuration B | No | Yes | Yes | Yes |
| 467 | Configuration C | No | No | No | Yes |

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A reagent test strip comprising:
   a. a top support layer comprising a sample aperture;
   b. a membrane comprising a reagent system for indicating the concentration of a target;
   c. a spreading layer;
   d. a bottom support layer comprising a measuring port in substantial alignment or approximate alignment with said sample aperture;
   wherein said membrane is affixed to said top support layer;
   further wherein said membrane is positioned between said top support layer and said bottom support layer;
   further wherein said spreading layer is positioned above said top support layer and in substantial or approximate alignment with said sample aperture; and
   further wherein a fluid applied to said spreading layer, passes through said sample aperture and contacts said membrane.

2. A reagent test strip according to claim 1 wherein said membrane is hydrophilic.

3. A reagent test strip according to claim 1 wherein said membrane is able to substantially exclude red blood cells.

4. A reagent test strip according to claim 1 wherein said membrane is a symmetric membrane or an asymmetric membrane.

5. A reagent test strip according to claim 1 wherein said membrane comprises polysulfone, polyethersulfone, nylon, or nitrocellulose.

6. A reagent test strip according to claim 1 wherein said reagent system comprises an enzyme.

7. A reagent test strip according to claim 6 wherein said enzyme is glucose oxidase.

8. A reagent test strip according to claim 6 wherein said enzyme is horseradish peroxidase.

9. A reagent test strip according to claim 1 wherein said reagent system comprises glucose oxidase and horseradish peroxidase.

10. A reagent test strip according to claim 1 wherein said reagent system comprises a substrate capable of forming a chromophore.

11. A reagent test strip according to claim 10 wherein said substrate is a AAP and MAOS.

12. A reagent test strip according to claim 10 wherein said chromophore is detected by measuring reflectance.

13. A reagent test strip according to claim 12 wherein said reflectance is indicative of the concentration of said target.

14. A reagent test strip according to claim 12 wherein said reflectance is detected directly on said membrane.

15. A reagent test strip according to claim 10 wherein said chromophore absorbs light from about 500 nm to about 800 nm.

16. A reagent test strip according to claim 10 wherein said chromophore absorbs light from about 600 nm to about 700 nm.

17. A reagent test strip according to claim 1 wherein said target is a biological moiety or chemical moiety.

18. A reagent test strip according to claim 1 wherein said target is a protein or nucleic acid.

19. A reagent test strip according to claim 1 wherein said target is glucose.

20. A reagent test strip according to claim 1 wherein said spreading layer is hydrophillic.

21. A reagent test strip according to claim 1 wherein said fluid comprises whole blood.

22. A reagent test strip according to claim 1, wherein said test strip reduces wet through of a said fluid through said membrane.

23. A reagent test strip comprising:
a. a top support layer comprising a sample aperture;
b. a membrane comprising a reagent system for indicating the concentration of a target;
c. at least one spacer able to reduce contact between said membrane and a surface; and
wherein said membrane is positioned below said top support layer and in substantial alignment or approximate alignment with said sample aperture.

24. A method of determining the presence or concentration of a target in a sample comprising the steps of:
a. applying a fluid suspected of comprising a target to the reagent test strip of claim 1;
b. detecting the reflectance of said membrane through said measuring port; and
c. determining the presence or concentration of said target.

25. A method of determining the presence or concentration of a target in a sample according to claim 24 wherein the step of determining the presence or concentration comprises measuring the absorbance of a chromophore.

26. A method of determining the concentration of a target in a sample comprising the steps of:
a. detecting a dry strip reading from the reagent test strip of claim 1;
b. running a preprogrammed threshold loop instruction;
c. detecting a first reflectance measurement;
d. running a preprogrammed kinetic loop instruction;
e. determining the presence or concentration of the target;
wherein said threshold loop instruction comprises the steps of:
  detecting a threshold comparison measurement;
  comparing said threshold comparison measurement to a predetermined threshold value;
  repeating the loop until said threshold comparison measurement is less than or equal to said predetermined threshold value;
further wherein a fluid suspected of including a target is applied during the step of running said threshold loop instruction;
further wherein said kinetic loop instruction comprises the steps of:
  detecting a second reflectance measurement;
  comparing said first reflectance measurement to said second reflectance measurement;
  ending the loop if said comparison is less than or equal to a predetermined cutoff value;
  replacing the value of said first reflectance measurement with the value of said second reflectance measurement; and
  repeating the loop.

27. A method according to claim 26 wherein the step of determining the presence or concentration of said target comprises calculating the concentration using said second reflectance measurement.

28. A method of determining the concentration of a target in a sample comprising the steps of:
a. detecting a dry strip reading from the reagent test strip of claim 1;
b. running a preprogrammed threshold loop instruction;
c. detecting a first reflectance measurement;
d. running a preprogrammed kinetic loop instruction;
e. running a consecutive comparison instruction;
e. determining the presence or concentration of the target;
wherein said threshold loop instruction comprises the steps of:
  detecting a threshold comparison measurement;
  comparing said threshold comparison measurement to a predetermined threshold value;
  repeating the loop until said threshold comparison measurement is less than or equal to said predetermined threshold value;
further wherein a fluid suspected of including a target is applied during the step of running said threshold loop instruction;
further wherein said kinetic loop instruction comprises the steps of:
  detecting a second reflectance measurement;
  comparing said first reflectance measurement to said second reflectance measurement;
  ending the loop if said comparison is less than or equal to a predetermined cutoff value;
  replacing the value of said first reflectance measurement with the value of said second reflectance measurement; and
  repeating the loop;
further wherein said consecutive comparison instruction comprises the steps of:
  detecting a third reflectance measurement;
  comparing said second reflectance measurement to said third reflectance measurement;
  ending the consecutive comparison instruction if said comparison is less than or equal to said predetermined cutoff value;
  replacing the value of said first reflectance measurement with the value of said third reflectance measurement; and
  returning to the step of running a kinetic loop instruction.

29. A method of determining the concentration of a target in a sample comprising the steps of:
a. detecting a dry strip reading from the reagent test strip of claim 1;
b. running a preprogrammed threshold loop instruction;
c. beginning a predetermined time point such that a fixed time point may be reached;
d. detecting a first reflectance measurement;
e. running a preprogrammed kinetic loop instruction;
f. determining the presence or concentration of the target;
wherein said threshold loop instruction comprises the steps of:
  detecting a threshold comparison measurement;
  comparing said threshold comparison measurement to a predetermined threshold value;
  repeating the loop until said threshold comparison measurement is less than or equal to said predetermined threshold value;
further wherein a fluid suspected of including a target is applied during the step of running said threshold loop instruction;
further wherein said kinetic loop instruction comprises the steps of:
  detecting a second reflectance measurement;
  comparing said first reflectance measurement to said second reflectance measurement;
  ending the loop if said second reflectance measurement is less than or equal to a predetermined cutoff value or if said fixed time point is reached;

replacing the value of the first reflectance measurement with the value of the second reflectance measurement; and repeating the loop.

30. A method of determining the concentration of a target in a sample comprising the steps of:
   a. detecting a dry strip reading from the reagent test strip of claim 1;
   b. running a preprogrammed threshold loop instruction;
   c. beginning a predetermined time point such that a fixed time point may be reached;
   d. detecting a first reflectance measurement;
   e. running a preprogrammed kinetic loop instruction;
   f. running a consecutive comparison instruction;
   f. determining the presence or concentration of the target;
   wherein said threshold loop instruction comprises the steps of:
      detecting a threshold comparison measurement;
      comparing said threshold comparison measurement to a predetermined threshold value;
      repeating the loop until said threshold comparison measurement is less than or equal to said predetermined threshold value;
   further wherein a fluid suspected of including a target is applied during the step of running said threshold loop instruction;
   further wherein said kinetic loop instruction comprises the steps of:
      detecting a second reflectance measurement;
      comparing said first reflectance measurement to said second reflectance measurement;
      ending the loop if said second reflectance measurement is less than or equal to a predetermined cutoff value or if said fixed time point is reached;
      replacing the value of the first reflectance measurement with the value of the second reflectance measurement; and
      repeating the loop;
   further wherein said consecutive comparison instruction comprises the steps of:
      detecting a third reflectance measurement;
      comparing said second reflectance measurement to said third reflectance measurement;
      ending the consecutive comparison instruction if said comparison is less than or equal to said predetermined cutoff value or if said fixed time point is reached;
      replacing the value of said first reflectance measurement with the value of said third reflectance measurement; and
      returning to the step of running a kinetic loop instruction.

31. A method of determining the concentration of a target in a sample comprising the stops of:
   a. detecting a dry strip reading from the reagent test strip of claim 1;
   b. running a preprogrammed threshold loop instruction;
   a. beginning a predetermined time point such that a fixed time point may be reached;
   d. determining the presence or concentration of a target in a sample when said fixed time point is reached;
   wherein said threshold loop instruction comprises;
      detecting a threshold comparison value;
      comparing said threshold comparison value to a predetermined threshold value;
      repeating the loop until said threshold comparison value is less than or equal to said predetermined threshold value; and
   further wherein a fluid inspected of including a target is applied during the step of running said threshold loop instruction.

\* \* \* \* \*

UNITED STATES PATENT AND TRADEMARK OFFICE
CERTIFICATE OF CORRECTION

PATENT NO.   : 6,759,190 B2
DATED        : July 7, 2004
INVENTOR(S)  : Jinn-Nan Lin and Chia-Lin Wang It is certified that error appears in the above-identified patent and that said Letters Patent is hereby corrected as shown below:

Column 22,
Line 33, change the word "inspected" to -- suspected --

Signed and Sealed this

First Day of February, 2005

JON W. DUDAS
*Director of the United States Patent and Trademark Office*